United States Patent [19]
McCaughey et al.

[11] Patent Number: 5,905,270
[45] Date of Patent: May 18, 1999

[54] APPARATUS FOR DETECTING THE PRESENCE OF A LIGHT ABSORBING GAS WITHIN AN ATMOSPHERE CONTAINING THE GAS

[75] Inventors: Ian McCaughey; Peter Frederick Mikkelsen, both of Sydney, Australia

[73] Assignee: Gas Tech Australia PTY Limited, Warriewood, Australia

[21] Appl. No.: 08/849,600

[22] PCT Filed: Nov. 29, 1995

[86] PCT No.: PCT/AU95/00800

§ 371 Date: Jun. 2, 1997

§ 102(e) Date: Jun. 2, 1997

[87] PCT Pub. No.: WO96/17239

PCT Pub. Date: Jun. 6, 1996

[30] Foreign Application Priority Data

Dec. 2, 1994 [AU] Australia .................. PM9820

[51] Int. Cl.⁶ .................................. G01N 21/61
[52] U.S. Cl. .................. 250/573; 356/51; 250/343
[58] Field of Search ............ 250/339.01, 339.03, 250/339.12, 341.1, 343, 351, 564, 573; 356/51, 436, 437

[56] References Cited

U.S. PATENT DOCUMENTS

5,070,244  12/1991  Simpson ..................... 356/51
5,369,278  11/1994  Lehto ........................ 356/311

*Primary Examiner*—Stephone B. Allen
*Attorney, Agent, or Firm*—Townsend and Townsend and Crew LLP

[57] ABSTRACT

A gas detector for detecting the presence of a light absorbing gas within an atmosphere (10) containing the gas includes a light source (12), a detector (14) arranged to detect a presence of incident radiation from the light source (12) and to provide an output signal (46) representative of the level of incident radiation from the light source (12). Electronic circuitry (130) is arranged to process the output signal (46) to provide an indication of the incident radiation. A power supply (40, 36) for cyclically energizing the light source (12) is also provided. The power supply is arranged to deliver substantially constant power at the or each level of energization of the light source (12).

10 Claims, 9 Drawing Sheets

APPARATUS FOR DETECTING THE PRESENCE OF A LIGHT ABSORBING GAS WITHIN AN ATMOSPHERE CONTAINING THE GAS

TECHNICAL FIELD

This invention relates to a method of and apparatus for detecting the presence of a light absorbing gas within an atmosphere containing the gas.

The invention has application to the detection of a combustible, toxic or other light absorbing gas, and the invention is hereinafter described in the context of detecting the presence of infra-red absorbing combustible gas in air. However, it will be understood that the invention does have broader application, to detection of the presence of any light absorbing gas in an atmosphere containing or consisting of any other gas. It will also be understood that the term "light absorbing gas" means a gas which characteristically absorbs radiation falling within the infra-red, visible and ultra-violet regions of the electromagnetic spectrum, and that the terms "radiation source" and "light source" mean a source which, when energised, emits radiation falling within the infra-red, visible and ultra-violet regions of the electromagnetic spectrum.

BACKGROUND OF THE INVENTION

The presence of hydrocarbon gas in air is conventionally monitored by beaming infra-red radiation through a chamber containing the gas-air mixture and detecting for absorption, or the degree of absorption, of radiation within the chamber. An output signal is derived which provides a measure of the amount of infra-red radiation that impinges on a detector, with an increase in the level of the output signal signifying a reduction in the amount of infra-red absorbing gas within the chamber. A bandpass filter is normally located between the radiation source and the detector to permit selective detection of the presence of a specific gas, that is a gas which absorbs radiation having a frequency in the filter pass band.

Determination of the volumetric proportion of hydrocarbon gas in air is determined by comparing a measured level of the output signal with a reference level, whilst accommodating variables introduced by ambient temperature change, component heat contributions, drifting of source and detector sensitivity, and accumulation of pollutants on optical elements within the system. One of the steps taken toward accommodating variables has involved driving the infra-red source by a square wave voltage, typically at a rate in the range of 0.5 to 50 Hz, and thermal drifts have been accommodated by measuring the peak-to-peak value of the output signal.

SUMMARY OF THE INVENTION

It has now been determined by the applicant that performance stability may be improved and the effect of variables may more readily be accommodated by driving the radiation source from a power supply which delivers substantially constant power at the or each level at which the radiation source is energised. Thus, the applicant has become aware that the output of the radiation source varies with age induced variations in the structural/chemical characteristics and the applicant has determined that the aberrant behaviour may be improved by driving the source with constant power.

Thus, the invention may be defined broadly as providing an apparatus for detecting the presence of a light absorbing gas within an atmosphere containing the gas. The apparatus comprises a light source, a detector arranged to detect the presence of incident radiation from the source and to provide an output signal representative of the level of incident radiation, electronic circuitry arranged to process the output signal to provide an indication of incident radiation, and a power supply for cyclically energising the light source. The apparatus is characterised in that the power supply is arranged to deliver substantially constant power at the or each level of energisation.

The invention may be defined also in terms of a method of detecting for the presence of a light absorbing gas within an atmosphere containing the gas. The method comprises the steps of beaming radiation from a light source through a chamber containing the atmosphere and toward a detector which is arranged to provide an output signal which is representative of a level of radiation falling incident on the detector, and processing the output signal to provide a measure of the level of radiation falling incident on the detector. The light source is cyclically energised from a power supply and the method is characterised in that the power supply is operated to provide substantially constant power to the light source at the or each level of energisation of the light source.

The power supply for the light source may be arranged to effect ON-OFF switching of the light source and to deliver substantially constant power to the light source during the ON cycle. However, the applicant has found that benefits are derived from sustaining excitation of the light source and, therefore, the power supply for the light source is preferably arranged to effect cyclic switching of the light source between upper and lower positive levels. With this latter arrangement the power supply will be arranged to deliver substantially constant power at appropriate levels to the light source at each of the two operating levels.

It has been found that by driving the light source in the above defined manner, both the short term and the long term stability of the light source are preserved. This in turn has the effect of minimising both the short term and long term drift of the light source, due in part to the minimisation of aging effects in the light source.

Constant power to the light source is maintained at the or each required level by multiplying voltage signals which are representative of the voltage level applied to the source and the current level passing through the source, comparing the product level with a reference level and adjusting the voltage level to maintain equality of the product and reference levels.

As in the case of prior art detectors, the apparatus of the present invention will normally include a bandpass filter, located between the light source and the detector, to permit selective detection of a gas having a characteristic absorption in the filter pass band.

The chamber which houses the active elements of the apparatus is preferably constituted by a sintered metal casing, most preferably a sintered stainless steel casing and, when the apparatus is to be used in wet or humid conditions, the casing most preferably is coated with polytetrafluoroethylene (PTFE). The PTFE coating is applied to a thickness which is sufficient to reduce moisture surface tension and thereby inhibit flow of moisture through the interstices within the casing but which is not sufficient to inhibit flow of gas into and from the chamber.

BRIEF DESCRIPTION OF THE DRAWINGS

The invention will be more fully understood from the following description of a preferred embodiment of a gas detection apparatus as illustrated by way of example in the accompanying drawings. In the drawings.

DESCRIPTION OF THE PREFERRED EMBODIMENT

Figure 1:
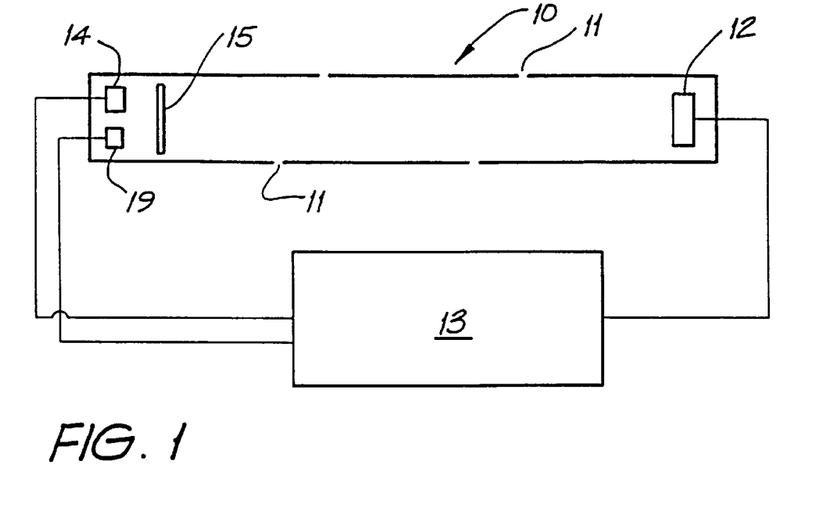
FIG. 1 shows a schematic representation of the complete gas detection apparatus.

As illustrated is FIG. 1, the apparatus in accordance with the preferred embodiment of the invention comprises a chamber 10 which is defined by a sintered stainless steel casing which is coated on its external surface with PTFE. The chamber 10 provides for the admission and through-passage of atmospheric gas which is to be tested or monitored for the possible inclusion of combustible hydrocarbon gas. Apertures 11 are shown in the apparatus as illustrated in FIG. 1 to represent interstices in the stainless steel casing through which the atmospheric gas may pass.

An infra-red radiation source 12, typically an incandescent lamp and hereinafter referred to as such, is located adjacent one end of the chamber 10 and is connected to associated electrical circuitry 13. The circuitry 13, described in more detail hereinafter, includes a power supply for the lamp 12 and the circuitry 13 provides for electronically controlled switching (ie, modulation) of the lamp output.

A pyroelectric detector 14 is located at the other end of the chamber 10, remote from the lamp 12, and functions normally to provide an output signal which is representative of the level of infra-red radiation falling incident on the detector 14.

Figure 2:
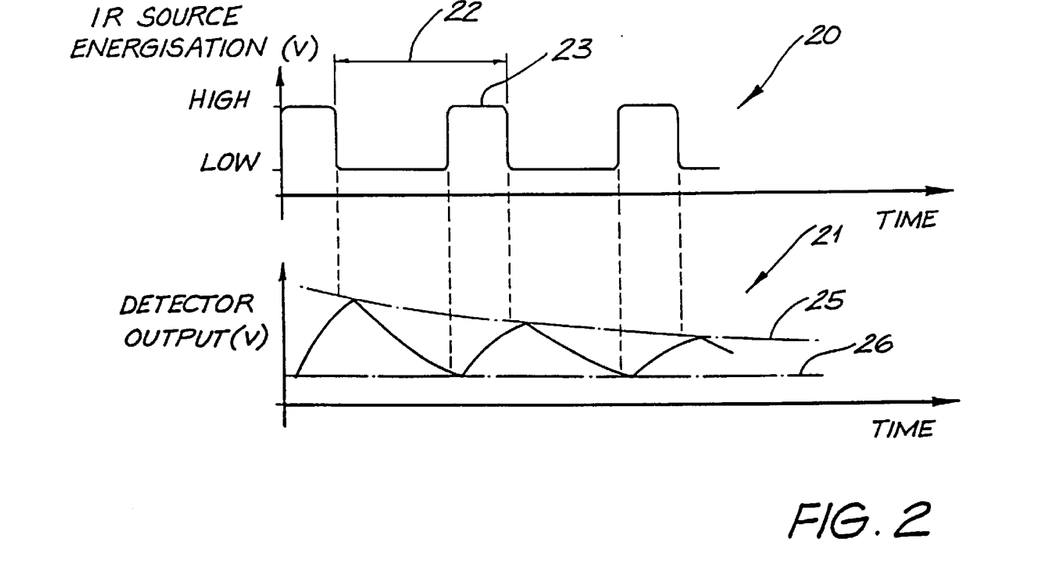
FIG. 2 shows graphically representations of energisation applied to an infra-red source within the apparatus and a typical output signal from a detector within the apparatus.
Figure 3:
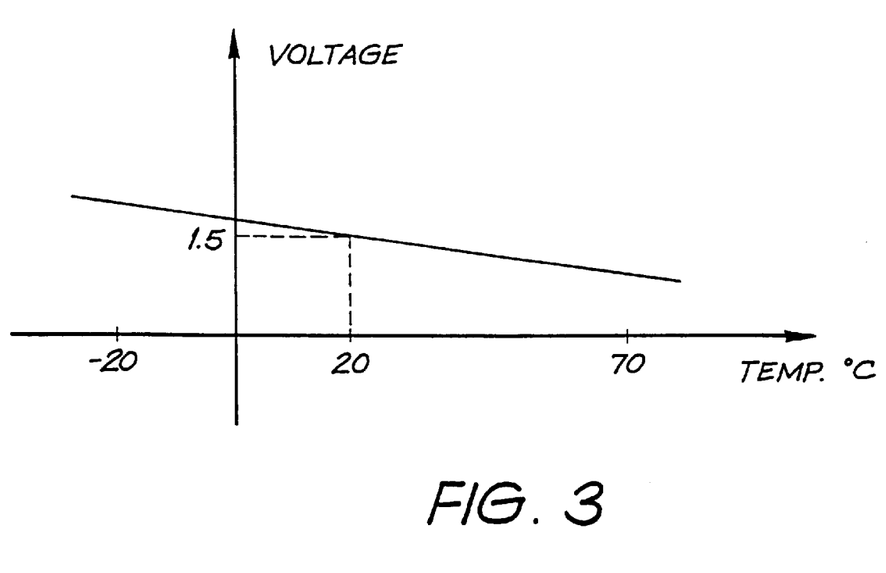
FIG. 3 shows a graphical representation of typical voltage drift caused by varying ambient temperature.

In FIG. 2, there is illustrated a lamp energisation graph 20 and corresponding detector output graph 21 for the system of FIG. 1. Each switching cycle eg. 22 preferably includes an 0.5 second HIGH period 23 in a total HIGH-LOW cycle 22 occupying 1.5 seconds. A typical output signal 21 is represented in FIG. 2 and the peak-to-peak measure of the approximately saw tooth wave form 21 of the detector output provides an instantaneous measure of the amount of infra-red radiation falling incident on the detector. As illustrated in FIG. 2, the falling level of output from the detector, represented by line 25 indicates a falling amount of infra-red radiation impinging on the detector 14 and, thus, indicates an increasing level of absorption of radiation (due to the increasing presence of absorbing gas) within the chamber 10. Any shift in the detector output level above zero, as indicated by line 26, is representative of background thermal radiation existing within the chamber 10 and the LOW level switching of the lamp. The level of background radiation will vary with temperature and FIG. 3 illustrates a graph of voltage versus temperature variation found in the detector 14 utilised in the preferred embodiment. As will be further described hereinafter, the circuitry 13 (FIG. 1) includes a compensator which compensates for any thermal drift of the line 26.

Turning again to FIG. 1, a bandpass filter 15 is located within the chamber 10 and is provided to pass selectively a range of frequencies to permit selective detection of gas having characteristic absorption in the filter pass band.

A stabistor 19 is mounted physically adjacent to the detector 14 and comprises two forward biased diodes, and exhibits a temperature variable characteristic similar to that exhibited by the detector 14 (the detector characteristic being illustrated in FIG. 3). The Stabistor 19 thereby provides an economical solution to monitoring the temperature induced drift in the detector 14, with the output of the Stabistor 19 being forwarded to the circuitry 13.

Figure 4:
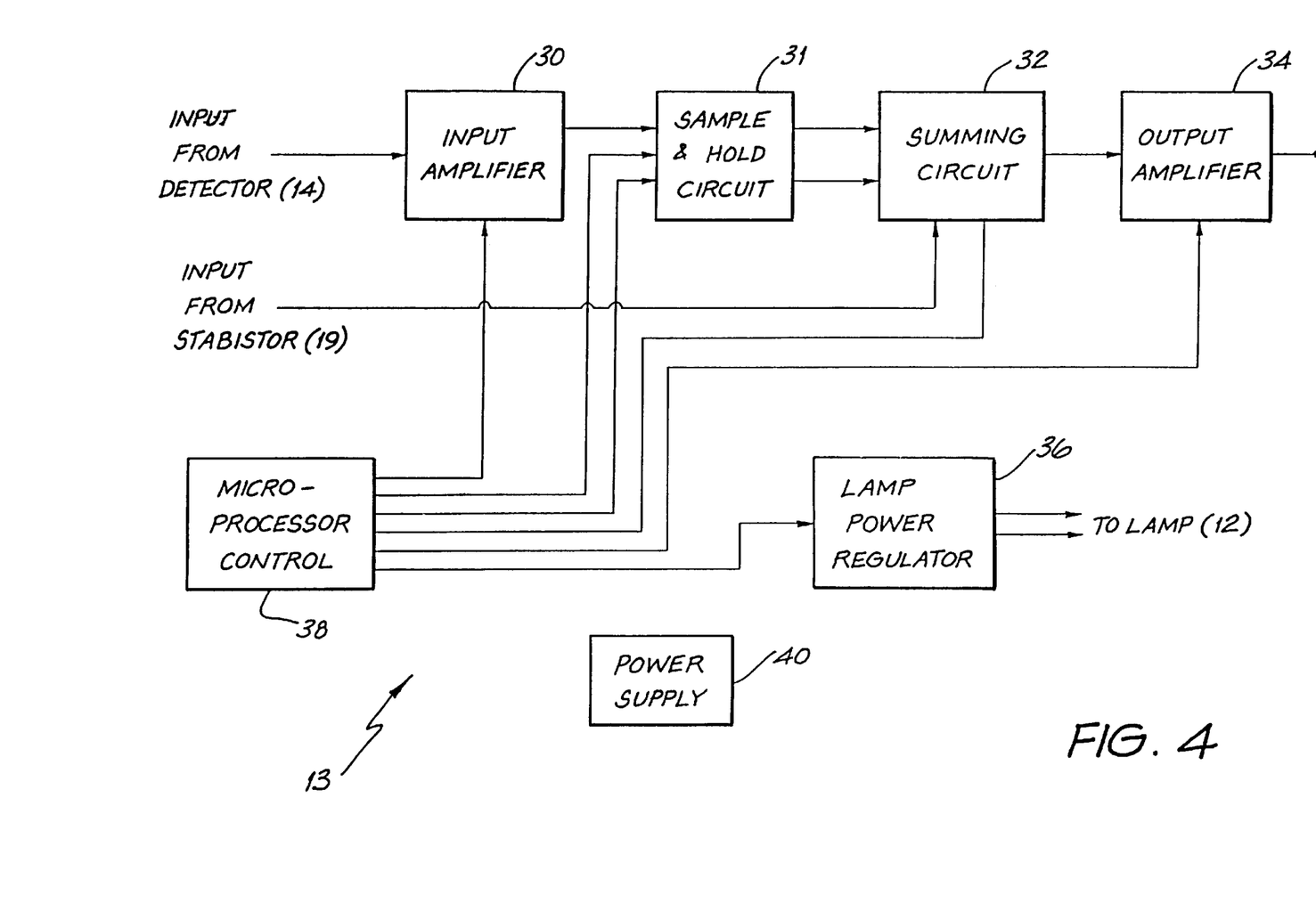
FIG. 4 shows in block diagrammatic form, the circuitry 13 of FIG. 1 in more detail.

Referring now to FIG. 4 there is illustrated, in block diagram form, the complex circuitry 13. The input from the detector 14 (FIG. 1) is first amplified 30 after which the peak-to-peak values are sampled 31. The samples are then analysed in summing circuit 32 and scaled by output amplifier 34.

A lamp power regulator circuit 36 is responsible for maintaining a constant power to the lamp 12 (FIG. 1) and, as will be further described hereinafter, operates via multiplication of a lamp current measure and a lamp voltage measure to maintain constant output power.

Microprocessor control circuit 38 is responsible for controlling the operation of the various portions of circuitry 13 and power supply 40 provides a regulated supply for circuitry 13 which mostly runs on an 8 volt power supply.

Figure 5:
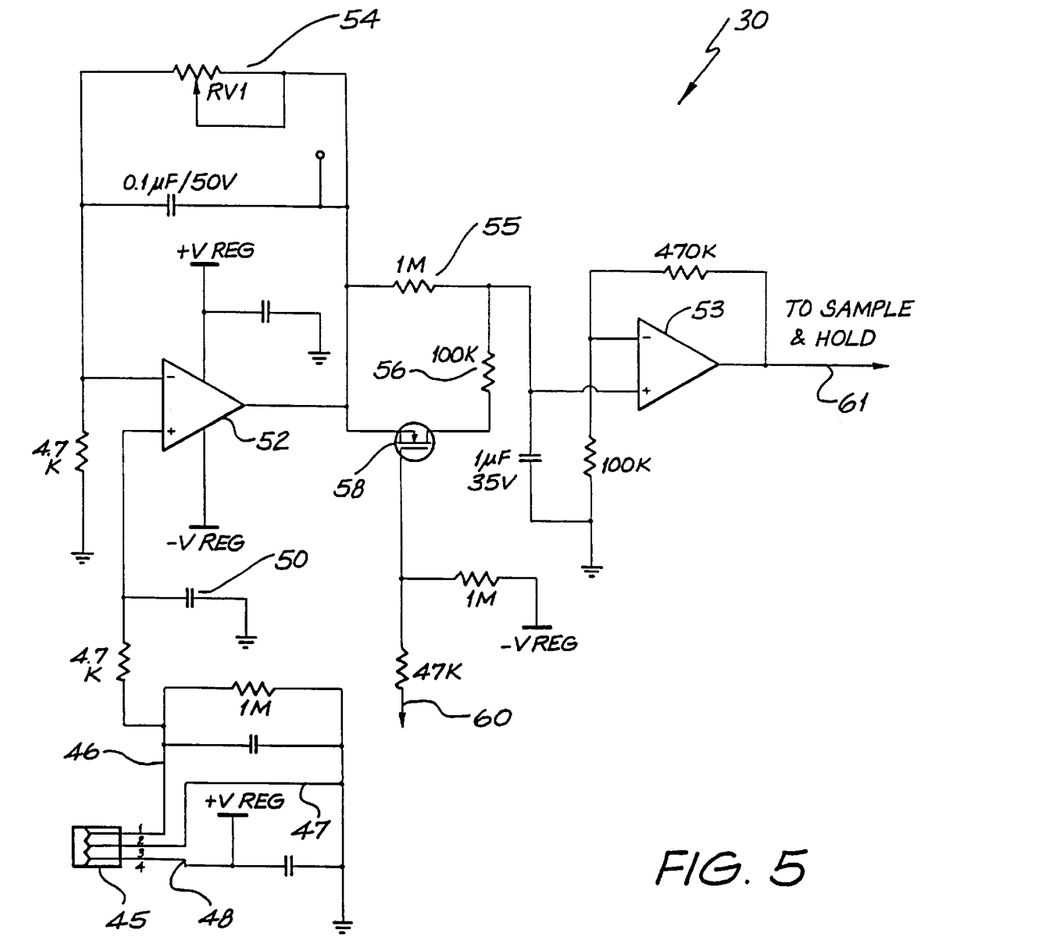
FIG. 5 illustrates a circuit for implementing the input amplifier of FIG. 4.

Referring now to FIG. 5, there is illustrated the input amplification circuit 30 in more detail. The input from the detector 14 (FIG. 1) includes a connector 45 which has a signal input 46, a ground line 47 and a positive power supply line 48.

As will be readily evident to those skilled in the art, the circuit-diagram of FIG. 5 and those which will be hereinafter disclosed in relation to other portions of circuitry 13 contain a number of filter circuits, for example capacitor 50, which are provided to filter any transients to ground and, as such, their operation need not be further herein discussed. Similarly, the provision of an 8 volt positive regulated voltage (+VREG) and the provision of a negative power supply (−VREG) will further be self evident to those skilled in the art.

The input signal 46 is amplified by amplifiers 52, 53 which are TLC272CD type amplifiers manufactured by Texas Instruments. The amplifiers are in cascade and the gain of the two stages is set to a predetermined level by variable control resistor 54.

A variable time constant filter is interposed between the two amplifiers and is formed by 1 MΩ resistor 55, 100 kΩ resistor 56, and 1 μF capacitor 57, in addition to transistor 58 which is a 2N7002 n-channel depletion MOSFET transistor type. The gate of the transistor 58 is connected to and controlled by the microprocessor control circuit 38 (FIG. 4) by means of lead 60. The output 61 of the amplifier circuit 30 is next fed to sample and hold circuit 31 (FIG. 4).

Figure 6:
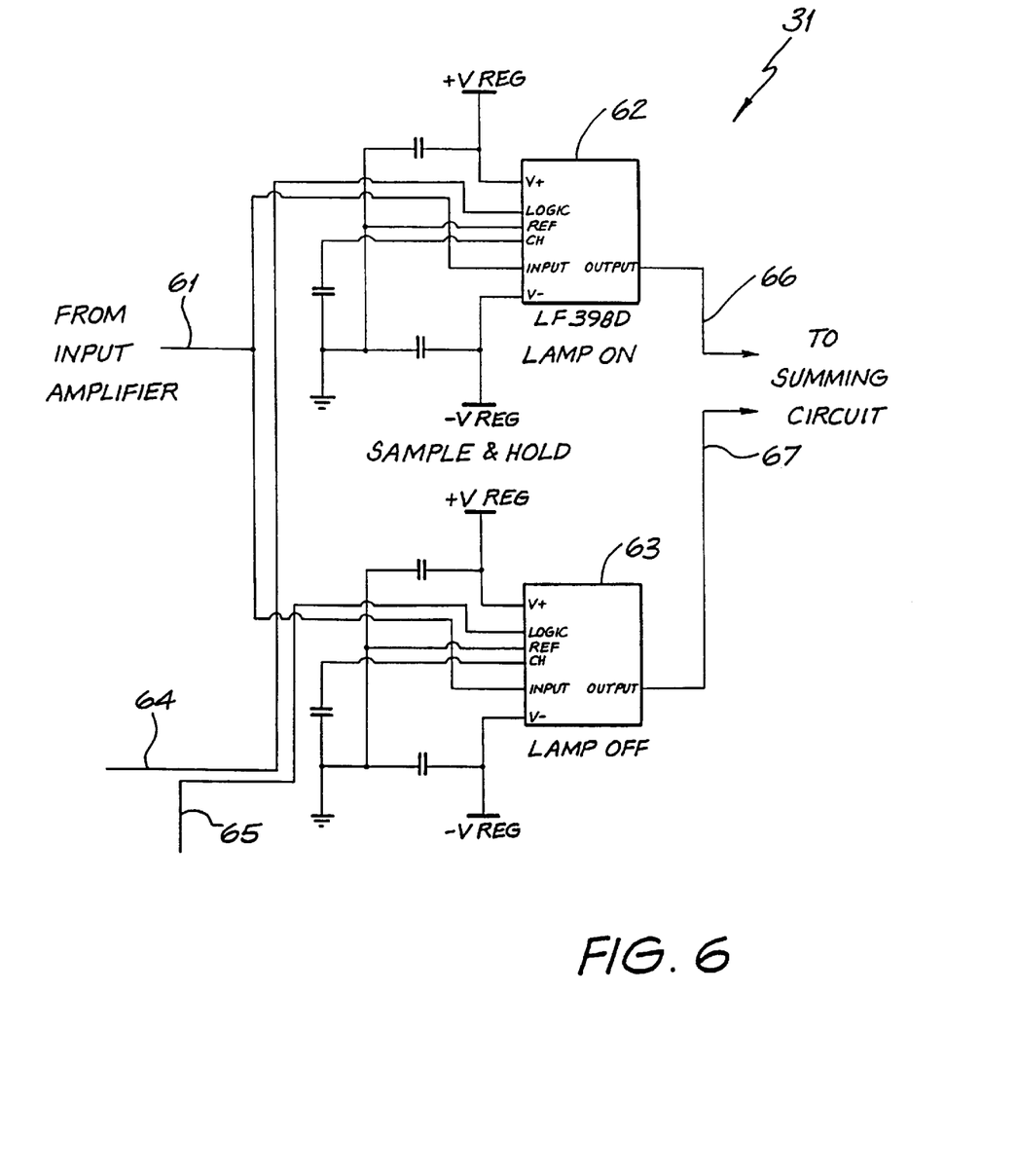
FIG. 6 illustrates a circuit implementing the sample and hold circuit of FIG. 4.

Turning now to FIG. 6, there is illustrated the sample and hold circuit 31 of FIG. 4 in more detail. The amplified detector input 60 has a structure substantially as depicted in detector output graph 21 (FIG. 2). The maximum detector value is sampled and latched by sample and hold 62 which can comprise a LF398D type sample and hold. The minimum value of amplified detector output 60 is sampled and latched by a similar sample and hold 63. The sample and holds 62 and 63 operate under control of the microprocessor control circuit 38 by means of signal lines 64, 65. The sample and hold control signals 64, 65 are accurately timed by the microprocessor to capture the signal 61 over a narrow time interval at the time of the lamp switching occurring. The sample and hold outputs 66, 67, which represent the high and low output values of the detector output, are forwarded to the summing circuit 32 of FIG. 4.

Figure 7:
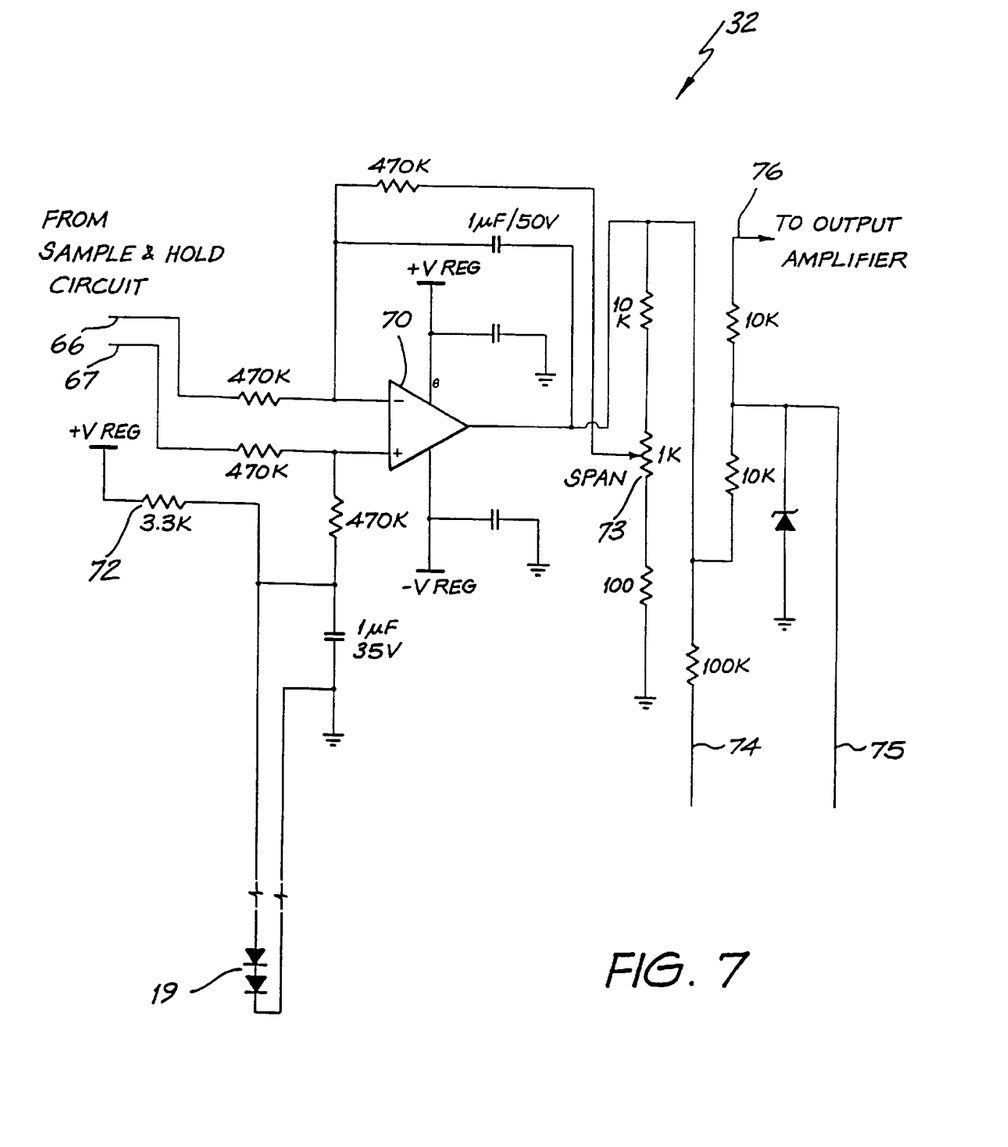
FIG. 7 illustrates, in more detail, the summing circuit of FIG. 4.

Turning now to FIG. 7, there is shown the summing circuit 32 of FIG. 4 in more detail. The two inputs 66, 67 from the sample and hold circuit 31 are input to differential amplifier 70 which subtracts the sample and hold values to determine the peak-to-peak value of the infra-red amplifier detector output. From the input 67 is also subtracted a reference voltage which is derived from the Stabistor 19 (located adjacent the detector 14 (FIG. 1)) which has been forward biased by resistor 72. The gain of the amplifier 70 is adjusted by variable resistor 73 so that the subtraction carried out by the differential amplifier gives a zero voltage output from amplifier 70 in the absence of infra-red absorbing gas. In the presence of gas, the infra-red absorption reduces the detector output which causes an increase in the output from amplifier 70.

The output from the amplifier is sampled 74 by the microprocessor circuit 38 in addition to being further adjusted 75 by the microprocessor circuit before being forwarded 76 to output amplifier 34.

Figure 8:
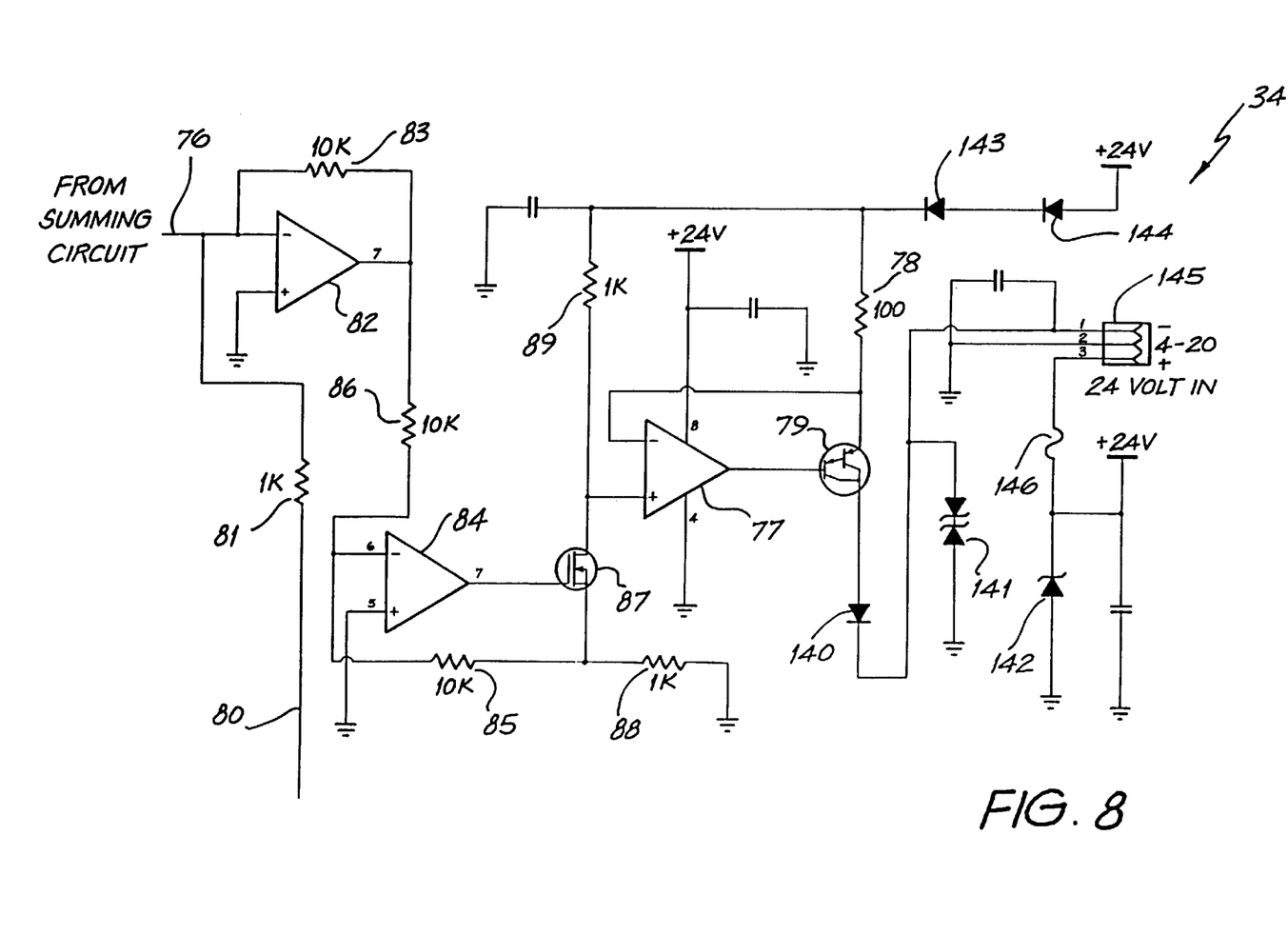
FIG. 8 illustrates the electrical circuitry implementing the output amplifier of FIG. 4.

Referring now to FIG. 8, there is shown output amplifier 34 in more detail. The compensated input 76 is subjected to even a further level of compensation via microprocessor input 80 which passes through resistor 81. As will be described hereinafter, the input 80 allows the microprocessor control circuit 38 (FIG. 4) to determine the local ambient temperature and calculate an additional correction to the output 76, based on a knowledge of the residual thermal drift of the system 13 after the above analogue compensation has been applied. This additional compensation may be set to typical values or, for more accuracy, can be individually calibrated.

The microprocessor input 80 is applied to resistor 81 and causes a proportional current to flow into the input of amplifier 82. This current is summed from the current from the summing circuit 31 via input signal 76. The summed current is converted to a corresponding amplified voltage by resistor 83 and amplifier 82.

An amplifier 84 and resistors 85, 86 convert the voltage output of amplifier 82 to a corresponding current at the drain of transistor 87, the current being proportional to the output voltage of amplifier 82 divided by resistor 88. The current through transistor 87 develops a corresponding voltage across resistor 89. Amplifier 77, resistor 78 and transistor 79 convert the voltage across resistor 89 to a corresponding current at the collector output of transistor 79. The current flowing in the collector of transistor 79 is the current flowing in the drain of transistor 87 multiplied by the ratio of resistor 89 to resistor 83. The output of transistor 79 is forwarded to an output plug 145 for subsequent monitoring. Diode 140 is a protective diode to prevent reverse current flow in the case of incorrect external connection of output lead 145. Diodes 141–144 are inserted to protect against transients and fuse 146 also serves a similar purpose. The output 145 can be connected to metering equipment for the monitoring of gases within chamber 10 (FIG. 1).

Figure 9:
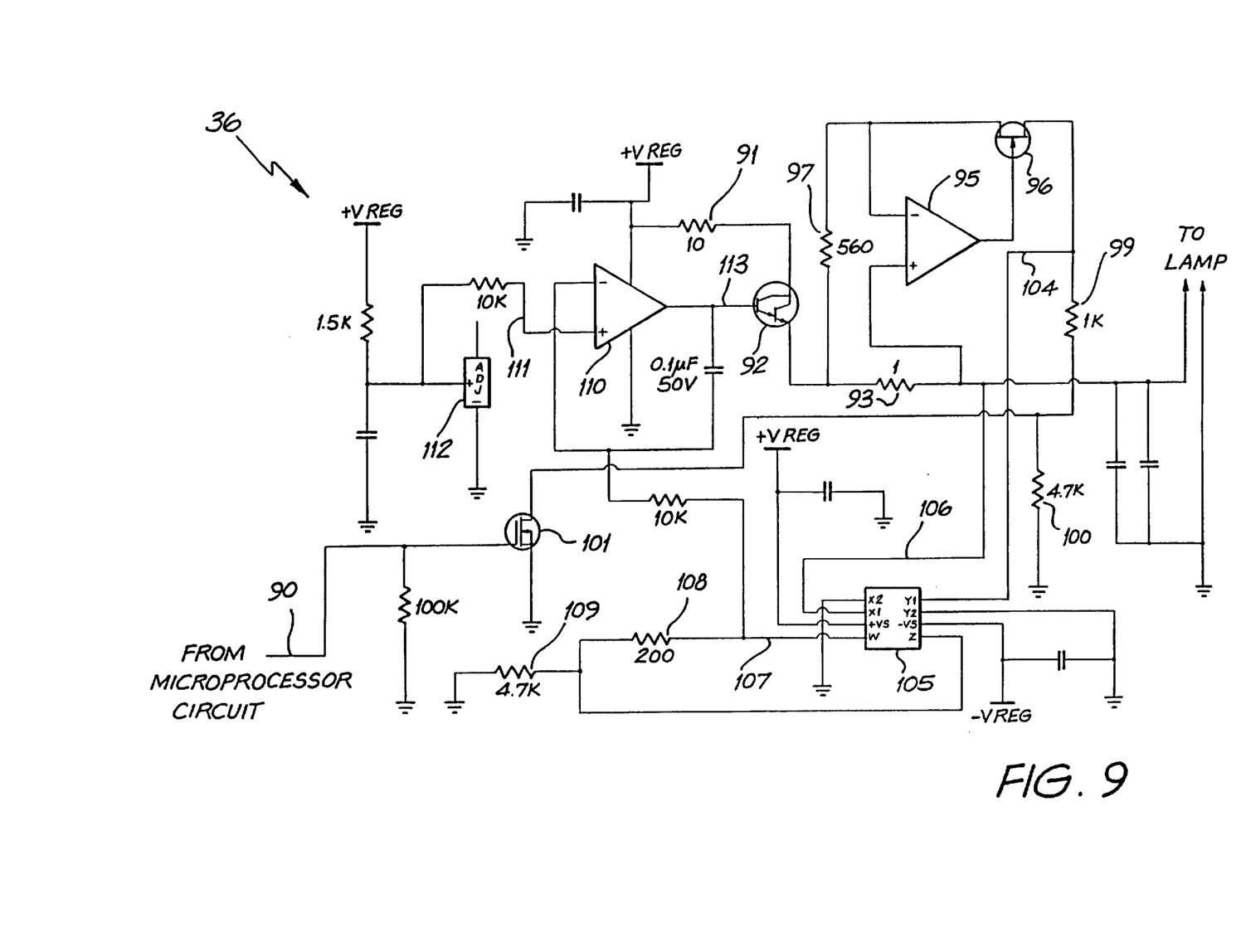
FIG. 9 illustrates the circuitry implementation of the lamp power regulator of FIG. 4.

Turning now to FIG. 9, there is illustrated the lamp power regulator 36 of FIG. 4 in more detail. An input go from the microprocessor control circuit 38 comprises the input clock to the lamp power regulator circuit 36 and has a periodic clocking structure substantially in accordance with that illustrated by lamp energisation graph 20 (FIG. 2). The input 90 is utilised to drive transistor 101 to either an OFF or ON state.

The current flow to the output lamp is through resistor 91, transistor 92 and resistor 93 where transistor 92 is the controlling active component. The current through resistor 93 is sensed by amplifier 95 and resistor 97. The output of transistor 96 is the sensed lamp current divided by the ratio of resistors 97 and 93. Resistor 97 is a 560 Ω resistor and resistor 93 is a 1 Ω resistor. Therefore, the drain current of transistor 96 will be equivalent to the lamp current divided by 560. This current develops a voltage across resistors 99 and 100 when transistor 101 is not conducting, ie. the voltage bridge will be developed when the input signal 90 from the microprocessor circuit is low. When the input 90 from the microprocessor circuit is high, transistor 101 will be conducting and the main voltage drop will be across resistor 99. The voltage at point 104 is sensed and forms a first Y input to an analogue multiplier 105. The lamp voltage is also sensed by means of signal 106 which forms a second X input to the analogue multiplier 105. The analogue multiplier can be an AD633JR type multiplier manufactured by Analog Devices.

The output 107 of the multiplier is then the product of the two inputs 106 and 104. This will be the product of the lamp voltage and a voltage proportioned to the lamp current. Hence the output 107 is proportional to the lamp power. In the preferred embodiment, the two resistors 108, 109 adjust the portionality constant such that the output 107 is 1.2 volts for the desired lamp power.

Amplifier 110 compares the output 107 with a precisely adjusted 1.2 volt reference 111 created via precision reference 112 and forms amplifier output 113 which is utilised to control transistor 92 to maintain the output 107 constant at the same voltage. The output level 107 will therefore be maintained constant while the power can be set at two values determined by transistor 101. When transistor 101 is ON, the lamp is at a maximum power, and when transistor 101 is off, the lamp power is decreased by 5.7 times for the particular resistor values 99,100 chosen. In this way, as mentioned previously, the lamp power is maintained substantially constant at each of two levels by the controlling gate 101, under the control of the microprocessor circuit 38.

Figure 10:
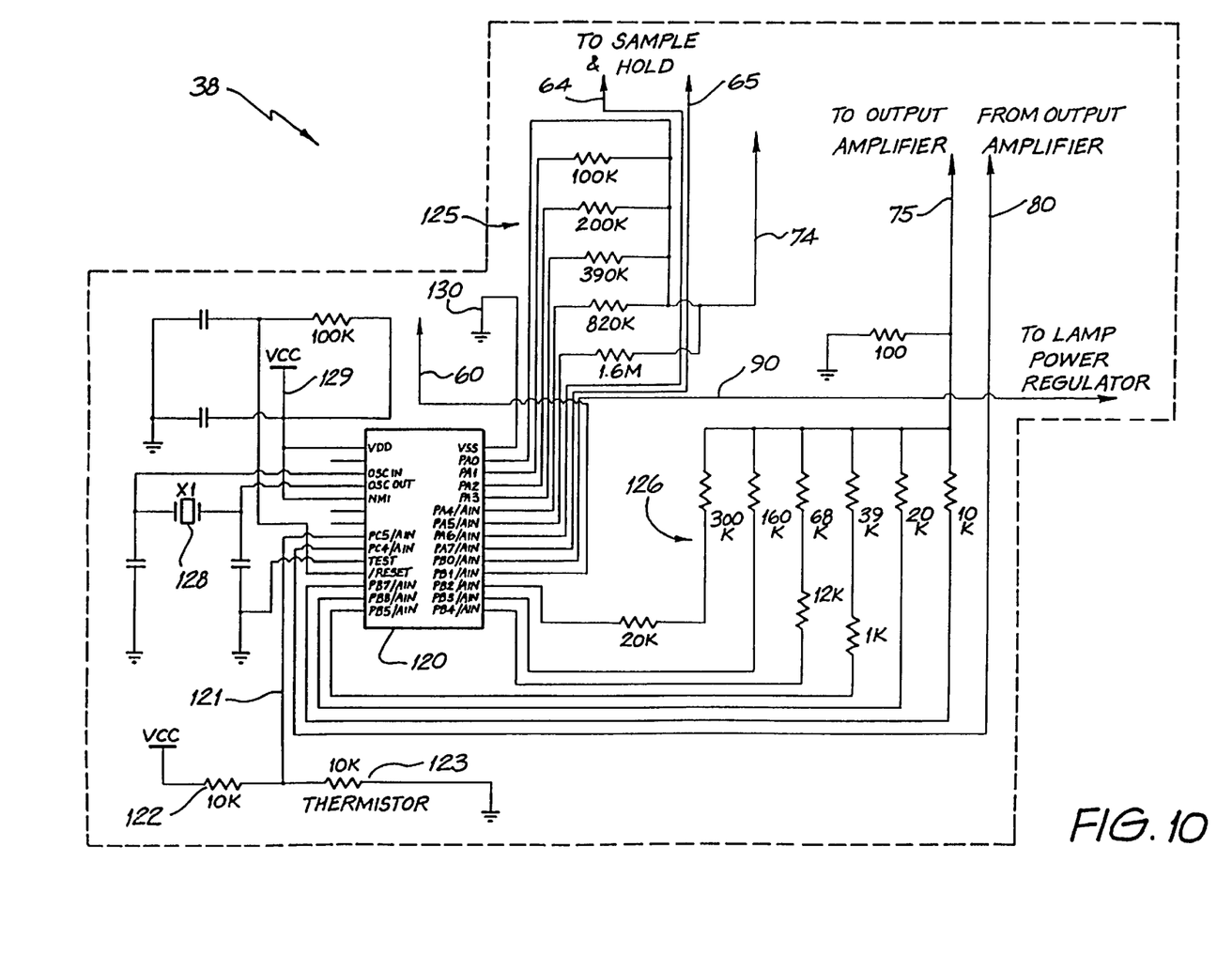
FIG. 10 illustrates the circuitry implementation of the microprocessor control circuit of FIG. 4.

Referring now to FIG. 10, there is illustrated the microprocessor control circuit 38 of FIG. 4 in more detail. The microprocessor control circuit is based around a ST62T25M6 microprocessor from SGS-Thomson micro electronics which includes a substantial number of analogue input/outputs (AIN). One of the inputs 121 is connected to a voltage bridge formed by resistor 122 and thermistor 123. This allows the microprocessor 120 to determine the local ambient temperature and to calculate any additional correction for forwarding to the output amplifier, based on the knowledge of the residual thermal drift of the circuitry 13 after the aforementioned analogue compensations have been applied. This additional compensation by microprocessor 120 may be set to a predetermined value or, for more accuracy, can be individually calibrated. The microprocessor output 60 is utilised to control the input amplifier circuit 30.

Two further outputs of the microprocessor 120 are connected to the sample and hold control line 64 and 65 for controlling the sample and hold latches 62, 63. The outputs of microprocessor 120 denoted PA0–PA5 are utilised, with resistor network 125, to form a digital analogue conversion circuit in the usual manner to finely tune the output level of signal 74 under the control of microprocessor 120. A second resistor network 126 is provided for fine tuning of the output level of output signal 75. Signal 80, is also provided as an input from the output amplification stage to microprocessor 120.

The usual oscillator 128 in addition to VCC circuit 129 and ground 130 are also provided as inputs to microprocessor 120.

The microprocessor 120 implements the lamp clocking scheme illustrated in FIG. 2 by means of output 90 to the lamp power regulator 36.

Referring again to FIG. 4, there is also provided the various power supply requirements 40 for the circuit 13. Power supply 40 is implemented in the usual manner to provide +VREG (8 volts), VCC (5 volts) and −VREG (−8 volts).

The foregoing describes only one embodiment of the present invention, modifications, obvious to those skilled in the art, can be made thereto without departing from the scope of the invention.

We claim:

1. An apparatus for detecting the presence of a light absorbing gas within an atmosphere containing the gas, the apparatus comprising a light source, a detector arranged to detect a presence of incident radiation from the light source and to provide an output signal representative of the level of incident radiation, electronic circuitry arranged to process the output signal to provide an indication of the incident radiation, and a power supply for cyclically energizing the light source to at least two distinct voltage energization levels, the power supply being arranged to further deliver substantially constant power to said light source at each level of energization.

2. An apparatus as defined in claim 1, wherein the power supply for the light source is arranged to effect cyclic switching of the light source between upper and lower positive levels and where the power supply is arranged to deliver substantially constant power to the light source at each of the levels of energisation.

3. An apparatus as claimed in claim 1, wherein said electronic circuitry further comprises thermal compensation means to correct said output signal for temperature variations of said detector.

4. An apparatus as claimed in claim 3, wherein said thermal compensation means includes a temperature sensor means substantially adjacent said detector.

5. An apparatus as claimed in claim 1, wherein said electronic circuitry includes an ambient temperature correction means adapted to correct said output signal for ambient temperature variations.

6. An apparatus as claimed in claim 1, wherein said electronic circuitry and said power supply are controlled and monitored by a microprocessor means.

7. An apparatus as claimed in claim 1, wherein said atmosphere is contained within a sintered metal casing having a predetermined number of interstices defined therein for allowing a flow of said gas.

8. An apparatus as claimed in claim 7, wherein said casing is coated with polytetra fluoroethylene.

9. A method of detecting for the presence of light absorbing gas within an atmosphere containing the gas, the method comprising the steps of beaming radiation from a light source through a chamber containing the atmosphere and toward a detector which is arranged to provide an output signal which is representative of a level of radiation falling incident on the detector, and processing the output signal to provide a measure of the level of radiation falling incident on the detector, the light source being cyclically energized from a power supply to at least two distinct voltage energization levels and the power supply further being operated to provide substantially constant power to the light source at each level of energization of the light source.

10. A method as claimed in claim 9 further comprising the step of correcting said output signal for thermal variations in said detector.

* * * * *